(12) United States Patent
Hefzi et al.

(10) Patent No.: US 12,378,573 B2
(45) Date of Patent: Aug. 5, 2025

(54) ASPARAGINASE BASED SELECTION SYSTEM FOR HETEROLOGOUS PROTEIN EXPRESSION IN MAMMALIAN CELLS

(71) Applicants: The Regents of the University of California, Oakland, CA (US); Technical University of Denmark, Kongens Lyngby (DK)

(72) Inventors: Hooman Hefzi, Cambridge, MA (US); Nathan E. Lewis, San Diego, CA (US); Karen Julie la Cour Karottki, Cambridge, MA (US); Helene Faustrup Kildegaard, Værløse (DK)

(73) Assignees: The Regents of the University of California, Oakland, CA (US); Technical University of Denmark, Kongens Lyngby (DK)

( * ) Notice: Subject to any disclaimer, the term of this patent is extended or adjusted under 35 U.S.C. 154(b) by 495 days.

(21) Appl. No.: 17/738,896

(22) Filed: May 6, 2022

(65) Prior Publication Data
US 2022/0356488 A1    Nov. 10, 2022

Related U.S. Application Data

(60) Provisional application No. 63/184,909, filed on May 6, 2021.

(51) Int. Cl.
| | | |
|---|---|---|
| *C12N 15/85* | (2006.01) | |
| *C07K 14/705* | (2006.01) | |
| *C12N 9/00* | (2006.01) | |
| *C12N 9/82* | (2006.01) | |
| *C12N 15/52* | (2006.01) | |
| *C12N 15/90* | (2006.01) | |
| *C12P 21/00* | (2006.01) | |
| *C12P 21/02* | (2006.01) | |

(52) U.S. Cl.
CPC ........ *C12N 15/85* (2013.01); *C07K 14/70578* (2013.01); *C12N 9/82* (2013.01); *C12N 9/93* (2013.01); *C12N 15/52* (2013.01); *C12N 15/907* (2013.01); *C12P 21/00* (2013.01); *C12Y 305/01001* (2013.01); *C12Y 603/01002* (2013.01); *C07K 2319/30* (2013.01); *C12N 2510/02* (2013.01); *C12N 2510/04* (2013.01); *C12N 2800/40* (2013.01); *C12N 2800/80* (2013.01); *C12N 2999/007* (2013.01)

(58) Field of Classification Search
CPC .... C12N 9/82; C12N 9/92; C12Y 305/01001; C12Y 603/01002
See application file for complete search history.

(56) References Cited

PUBLICATIONS

Li, F., Vijayasankaran, N., Shen, A. (Yijuan), Kiss, R., & Amanullah, A. (2010). Cell culture processes for monoclonal antibody production. mAbs, 2(5), 466-479. https://doi.org/10.4161/mabs.2.5.12720 (Year: 2010).*

Grav, L.M et al (2017). Application of CRISPR/Cas9 Genome Editing to Improve Recombinant Protein Production in CHO Cells. In: Meleady, P. (eds) Heterologous Protein Production in CHO Cells. Methods in Molecular Biology, vol. 1603. Humana Press, New York, NY. https://doi.org/10.1007/978-1-4939-6972-2_7 (Year: 2017).*

Pavlova NN, Hui S, Ghergurovich JM, Fan J, Intlekofer AM, White RM, Rabinowitz JD, Thompson CB, Zhang J. As Extracellular Glutamine Levels Decline, Asparagine Becomes an Essential Amino Acid. Cell Metab. Feb. 6, 2018;27(2):428-438.e5. doi: 10.1016/j.cmet.2017.12.006. Epub Jan. 11, 2018. (Year: 2018).*

* cited by examiner

*Primary Examiner* — Jennifer Dunston
*Assistant Examiner* — Alexandra Rose Lippolis
(74) *Attorney, Agent, or Firm* — Eversheds-Sutherland (US) LLP

(57) ABSTRACT

A non-naturally occurring cell comprising an inoperative genomic asparaginase (Aspg) gene and an inoperative glutamine synthetase (Gs) gene, wherein the cell has been transfected with a controllably expressed gene encoding an enzyme having asparaginase activity, a controllably expressed gene encoding an enzyme having glutamine synthetase activity, and a controllably expressed gene encoding a heterologous protein of interest.

20 Claims, 8 Drawing Sheets

ASPARAGINASE BASED SELECTION SYSTEM FOR HETEROLOGOUS PROTEIN EXPRESSION IN MAMMALIAN CELLS

CROSS REFERENCE

This application claims the benefit of U.S. Provisional Application No. 63/184,909 filed May 6, 2021, which application is incorporated herein by reference in its entirety.

TECHNICAL FIELD

The present invention relates to modified cells used for the production of recombinant proteins.

BACKGROUND

Chinese hamster ovary (CHO) cells are the most used cell line for biopharmaceutical production (Walsh 2018). The exploitation of effective selection systems such as those based on dihydrofolate reductase (Dhfr) and methotrexate (MTX) or glutamine synthetase (Gs) and methionine sulfoximine (MSX) have greatly contributed to improved production of heterologous proteins. Furthermore, double selection with both systems improved production even further (Li et al. 2010). Other selection systems have been proposed, such as transient depletion of vitamin B5 (Pourcel et al. 2020). However, there is a need for further enhancing CHO expression systems.

SUMMARY OF THE INVENTION

The disclosure provides non-naturally occurring cells for expression of recombinant proteins and other research.

The invention provides a selection system for heterologous protein expression in mammalian cell (e.g., Chinese hamster ovary (CHO) cells). The selection system is based on knocking out the asparaginase (Aspg) gene and transfecting with an expression vector containing Aspg and a heterologous protein of choice. This system is combined with the glutamine synthetase (Gs) selection system to boost the specific productivity of the heterologous protein and relies on the same selective pressure (i.e., growth in medium lacking glutamine).

The invention provides a selection system for heterologous protein expression using Aspg. Coselection with Aspg and Gs vectors in a Gs knockout cell line leads to slightly increased specific productivity while coselection with Aspg and Gs vectors in a Gs/Aspg double knockout cell line leads to markedly increased specific productivity, in both cases compared to the industry standard selection with a Gs vector in a Gs knockout cell line. It is unexpected that the double selection would produce such a strong increase.

The invention provides that loss of Asparaginase (Aspg), the enzyme which catalyses the deamination of asparagine to aspartate, nearly eliminated growth in cells grown in media without glutamine. Therefore, Aspg can be used as a selective marker to enhance the selection system for a more potent selection of highly productive CHO cells. The addition of the Aspg selection system greatly enhanced the glutamine synthetase (Gs) system, leading to the generation of substantially higher productivity and titers in CHO cells.

BRIEF DESCRIPTION OF THE DRAWINGS

In FIG. 5A and FIG. 5B, all cell lines were grown in three replicates; error bars represent standard deviation.

FIG. 5B shows titer in shake flask batch culture of the top minipool after adaptation.

DETAILED DESCRIPTION

Figure 1:
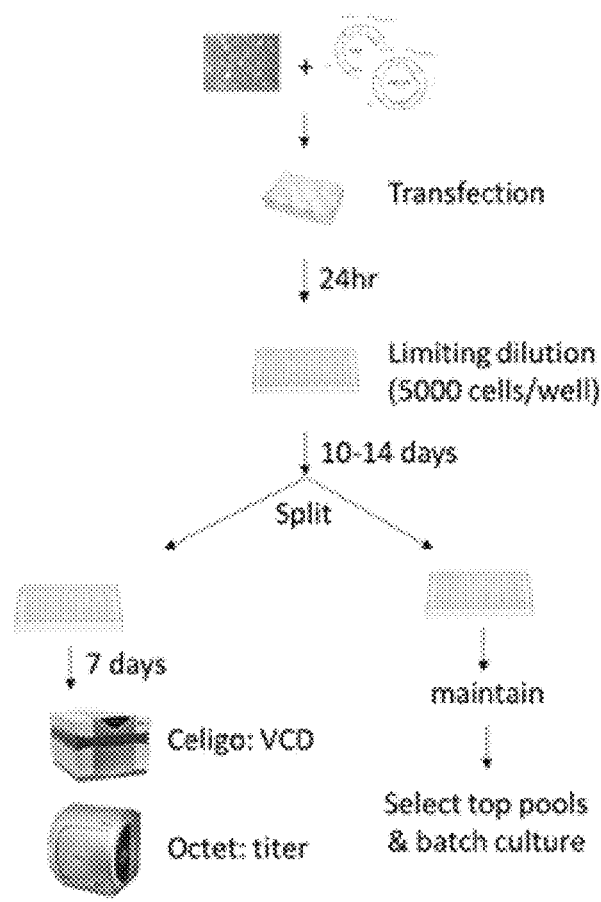
FIG. 1 shows an exemplary overview of minipool selection and batch culture.

The integration of exogenous DNA into cultured cells is often facilitated by co-introduction of the desired DNA alongside a selectable element and growth in the corresponding selective pressure (e.g., transfection of the desired gene+a gene imparting antibiotic resistance combined with growth in medium containing the antibiotic). In the biopharmaceutical industry, metabolic selection systems restoring nutritional prototrophies are routinely used to generate mammalian cell lines producing high quantities of life-saving biotherapeutic protein drugs. Dihydrofolate reductase (Dhfr) or glutamine synthetase (Gs) are the most commonly leveraged metabolic selectable markers (Cockett et al., 1990; Kaufman & Sharp, 1982). However, the cell line generation process using these is time-consuming and laborious, often requiring one (Gs) or several (Dhfr) rounds of gene amplification driven by the addition of inhibitory compounds (e.g., methotrexate and methionine sulfoximine) during selection as well as the screening of 100s to 1000s of clones to identify clones with the desired production and quality profiles. It has been shown that utilizing these two systems simultaneously increases the probability that a highly productive cell will be generated—as well as improving the maximum product titer (Li et al., 2010). Recent work has demonstrated the feasibility of additional metabolic selection systems in CHO (Budge et al., 2021; Capella Roca et al., 2019; Pourcel et al., 2020; Sun et al., 2020; Zhang et al., 2020) with one study (Zhang et al., 2022) showing that using 8 selectable markers simultaneously can significantly increase the productivity of the resulting cell lines (although the cells grew very slowly). The orthogonality of these new selection systems (e.g., each requiring the dropout of a different medium component for selective pressure) and/or need for multiple genetic edits led to exploration of whether it was possible to increase the selective stringency of glutamine deprivation in a more simple manner, enhancing the selective pressure of one of the most established tools in the clinical cell line generation workflow, without requiring changes from established selection conditions.

The present invention provides compositions, methods, and systems comprising a non-naturally occurring mammalian cell comprising an inoperative genomic asparaginase (Aspg) gene and an inoperative glutamine synthetase (Gs) gene, wherein the cell has been transfected with a controllably expressed gene encoding an enzyme with asparaginase activity, a controllably expressed gene encoding an enzyme with glutamine synthetase activity, and a controllably expressed gene encoding a heterologous protein of interest. In some embodiments, the gene encoding the enzyme with asparaginase activity is an Aspg gene. In some embodiments, the gene encoding the enzyme with glutamine synthetase activity is a Gs gene.

In embodiments, the invention provides that the cell has been immortalized. In some instances, an immortalized cell is one which has been manipulated or has otherwise mutated to proliferate indefinitely or for an extended period of time. In some instances, a culture of cells provided herein (e.g., an immortalized cell population) is able to continuously divide indefinitely, so long as adequate culture media is maintained (e.g., through perfusion of fresh media or by passing or splitting cell cultures to dilute cells and introduce fresh media). In some embodiments, the immortalized cell provided herein produces a stable culture for at least 2 weeks, at least 4 weeks, at least 8 weeks, at least 16 weeks, at least 26 weeks, at least 52 weeks, at least 2 years, or longer.

In embodiments, the cell of the instant invention is a mammalian cell. In some embodiments, the cell is derived from a primate, a feline animal, a canine animal, a bovine animal, a porcine animal, an ovine animal, a caprine animal, or a rodent. In some embodiments, the cell is derived from a human. Examples of human derived cells include human embryonic kidney cells (e.g., HEK293), lung cancer cells (e.g., A549), breast cancer cells (e.g., BHL-100), colon cancer cells (e.g., Caco02, HCT-15, HT-29), liver cancer cells (e.g., Chang), cervix carcinoma cells (e.g., HeLa), lymphoma cells (e.g., Jurkat), and the like. In some embodiments, the cell is a HEK293 or HeLa cell. In some embodiments, the cell is a rodent cell. In some embodiments, the cell is a mouse cell, a hamster cell, or a rat cell. Exemplary rodent cells include 3T6 cells, A9 cells, AtT-20 cells, BALB/3T3 cells, BHK-21 cells, CHO cells, Clone 9 cells, Clone M-3 cells, HaK cells, I-10 cells, Jensen cells, L2 cells, LLC-WRC-256 cells, McCoy cells, XC cells, Y-1 cells, and the like. In embodiments, the invention provides that the cell is a Chinese hamster ovary (CHO) cell.

In some embodiments, the cell of the instant invention is an adherent cell line. In some embodiments, gene knockout and transfection with the genes encoding the enzyme with glutamine synthetase activity or asparaginase activity (e.g., Gs and/or Aspg gene) occur with the cell or cells in an adherent format. In some embodiments, the cells are then adapted to a suspension culture. In some embodiments, the cell is in a suspension culture. Adaptation to a suspension culture can be performed using a wide variety of methods known in the art, including clonal isolation and transfer to suspension growth and culture conditions. Alternatively, transfection and/or gene knockout can also be performed in a suspension format. Once in a suspension culture format, the cells can be cultured using a wide variety of methods, including without limitation shake flask formats, batch bioreactors, and the like. In suspension culture, cells can be grown to a desired volume (e.g., at least 1L, at least 5L, at least 10L, at least 50L, at least 100L, or larger volumes for industrial scale production) and grown for a desired amount of time to achieve optimal expression and characteristics of the heterologous protein of interest. In addition to large volume suspension culture formats, large scale production of heterologous proteins of interest using the cells provided herein can also be accomplished using adherent cell formats, such as through use of fixed bed bioreactors, roller bottle formats, and the like. Cell cultures can be supplemented in a variety of methods to enhance protein production and cell survival, such as perfusion technologies to continuously provide fresh media to the culture.

In some embodiments, the cell includes one or more genes of the cell which have been modified. In some embodiments, one or more genes of the cell have been knocked-out or otherwise made inoperative. In some embodiments, knock-out genes are prepared by introducing one or more mutations into the gene such that the protein encoded by the gene is either not expressed or expressed in an inactive form. Non-limiting examples of gene modifications which can accomplish the knock-out include frameshift modifications (e.g., insertions or deletions of nucleotides which change the open reading frame of the gene), point mutations (e.g., substitution of one or more nucleotides such that the gene encodes a protein which contains a substituted amino acid which renders it inactive), deletion or modification of the start codon, insertion or deletion of one or more codons encoding amino acids of the encoded protein, and the like. In some embodiments, the modification includes deletion (e.g., excision) of the entire gene from the genome of the organism. In some embodiments, generating a knock-out of a given gene involves modification of both alleles of the gene.

In some embodiments, the cell comprises a knock-out of one or both of the asparaginase (Aspg) or glutamine synthetase (Gs) genes. The human asparaginase gene is described in GENBANK under Gene ID: 374569. The human glutamine synthetase gene is described in GENBANK under Gene ID: 2752. In embodiments, the invention provides that the Gs gene is a Glul gene. Analogous versions of these genes for different organisms (e.g., Chinese hamsters, such as in CHO cells) are well known in the art and available in public databases such as GENBANK.

Knock-out versions of genes as provided herein can be prepared using a variety of methods and/or gene editing systems well known in the art. Exemplary methods and gene editing systems are described in Gaj et al., Cold Spring Harb Perspect Biol. 2016 December; 8(12): a023754 doi:

10.1101/cshperspect.a023754. A gene editing system as provided herein is a system which comprises all the necessary components in order to effectuate the desired alterations into a target gene. In some embodiments, the gene editing system comprises exogenous functionalities which work with endogenous systems (e.g., host cell proteins implicated in homology directed repair) to effectuate the desired alteration to the desired allele.

In some embodiments, the gene editing system comprises a guide nucleic acid. In some embodiments, the gene editing system comprises a guide RNA. In some embodiments, the guide RNA is configured to recruit the endonuclease enzyme (e.g., CRISPR-Cas9 and derivatives thereof) in order to effectuate a cut in the desired gene.

In some embodiments, the gene editing system comprises an endonuclease. In some embodiments, the endonuclease is configured to perform a cut in the target gene. In some embodiments, the endonuclease is configured to perform a cut in the target gene when in complex with the guide RNA. In some embodiments, the endonuclease is selected from a meganuclease, a Transcription Activator Like Effector Nucleases (TALEN), a Zinc-Finger Nucleases (ZFN), and a Clustered Regularly Interspaced Short Palindromic Repeats (CRISPR)-associated system (Cas), and derivatives thereof. In some embodiments, the endonuclease is a meganuclease or a derivative thereof. In some embodiments, the endonuclease is a TALEN or a derivative thereof. In some embodiments, the endonuclease is a ZFN or a derivative thereof. In some embodiments, the endonuclease is a Cas or a derivative thereof. In some embodiments, the endonuclease is a Cas9 or a derivative thereof. In some embodiments, the gene editing system comprises a guide RNA and an endonuclease enzyme.

In some embodiments, the gene editing system comprises an exogenous nucleic acid (e.g., DNA) repair template configured to introduce a desired modification into the targeted gene. In some embodiments, the nucleic acid repair template comprises homology arms which overlap with the target gene and flank the target modification site.

In some embodiments, the gene editing system or a portion thereof is encoded in a vector. In some embodiments, the vector is a plasmid, a viral vector, a cosmid, or an artificial chromosome. In some embodiments, the vector is a plasmid, a viral vector, or a cosmid. In some embodiments, the vector is a plasmid or a viral vector. In some embodiments, the vector is a plasmid. In some embodiments, the vector is a viral vector. Examples of viral vectors include retrovirus, lentivirus, adenovirus, adeno-associated virus, herpes simplex virus, and the like. In some embodiments, all exogenous components of the gene editing system are encoded on vectors. In some embodiments, all components of the gene editing system are encoded on a single vector.

In some embodiments, a gene editing system is used to create a double knock-out of Aspg and Gs. In some embodiments, the cell is an Aspg and Gs double knock-out made with a gene editing system. In some embodiments, the gene editing system is meganuclease system, a TALEN system, a ZFN system, or a CRISPR-Cas system. In embodiments, the invention provides that the cell is an Aspg and Gs double knock-out made with a CRISPR-Cas9 system.

In some embodiments, the genes that have been knocked out or made inoperative (e.g., Aspg and/or Gs) are reintroduced into the cell, or genes encoding enzymes having substantially the same activity if the knocked out genes are reintroduced into the cell.

In some embodiments, a gene encoding an enzyme having asparaginase activity is transfected into the cell. In some embodiments, the asparaginase activity comprises the hydrolysis of 1-asparagine to 1-aspartic acid. In some embodiments, the enzyme having asparaginase activity has a non-asparaginase primary activity but retains some asparaginase activity. In some embodiments, the enzyme displays an asparaginase activity which is at least 1%, at least 5%, at least 10%, at least 20%, at least 30%, at least 40%, at least 50%, at least 60%, at least 70%, at least 80%, or at least 90% of the asparaginase activity of the asparaginase encoded by an Aspg gene.

In some embodiments, a gene encoding an enzyme having glutamine synthetase activity is transfected into the cell. In some embodiments, the glutamine synthetase activity comprises the condensation of glutamate and ammonia to form glutamine. In some embodiments, the enzyme having glutamine synthetase activity has a non-glutamine synthetase primary activity but retains some glutamine synthetase activity. In some embodiments, the enzyme displays a glutamine synthetase activity which is at least 1%, at least 5%, at least 10%, at least 20%, at least 30%, at least 40%, at least 50%, at least 60%, at least 70%, at least 80%, or at least 90% of the glutamine synthetase activity of the glutamine synthetase encoded by a Gs gene.

In some embodiments, Gs and Aspg genes are transfected into the cell. In some embodiments, the Gs and Aspg genes are transfected into the cell on one or more vectors. In some embodiments, the vector or vectors which re-introduce the Gs and Aspg genes are each independently selected from a plasmid, a viral vector, and a cosmid. In some embodiments, each of the Gs and Aspg genes are transfected into the cell on plasmids. In embodiments, the invention provides that the Gs gene and the Aspg gene are transfected into the cell on separate plasmids. In some embodiments, the Gs and Aspg genes are transfected into the cell on the same plasmid. When on the same plasmid, the Gs and Aspg genes can be controlled by the same promoter (e.g., the Gs and Aspg genes are separated by a self cleavage peptide, such as a T2A peptide), the same type of promoter (e.g., the Gs and Aspg genes are both controlled by SV40 promoter elements), or by two different promoters.

Figure 9:
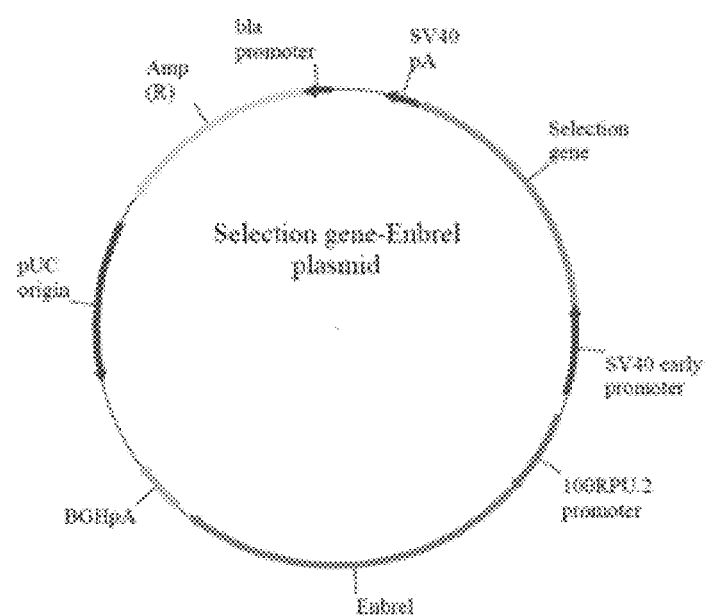
FIG. 9 shows a plasmid construct.

In some embodiments, one or more of the vectors which are transfected into the cell to reintroduce the knocked out genes (e.g., Gs and Aspg) further comprise the gene encoding the heterologous protein of interest. In some embodiments, the gene encoding the heterologous protein of interest is controlled by a different promoter than that which controls the Gs or Aspg gene. In some embodiments, the plasmid which comprises the Gs gene comprises the gene encoding the heterologous protein of interest. In some embodiments, the plasmid which comprises the Aspg gene comprises the gene encoding the heterologous protein of interest. In embodiments, the invention provides that each plasmid further comprises the gene encoding the heterologous protein of interest. An exemplary plasmid is shown in FIG. 9.

In some embodiments, the invention provides that the Gs and Aspg gene are transfected into the cell on separate plasmids and each of the plasmids also comprises the gene encoding the heterologous protein of interest. In some embodiments, the two plasmids are transfected into cells or a cell culture using a ratio of the two plasmids of approximately 1:1 (mol/mol). In some embodiments, an alternative ratio is used (e.g., a molar excess of the plasmid comprising the Gs gene). In some embodiments, the ratio of the two plasmids during the transfection step is from about 2:1 to about 1:2 (mol/mol) of the plasmid encoding the Gs gene to the plasmid encoding the Aspg gene.

The cells and systems provided herein are useful for the expression of heterologous proteins of interest. The heterologous protein of interest can be of a wide variety of types and used in a variety of applications. For example, in some embodiments, the heterologous protein of interest is an active pharmaceutical ingredient, a reagent in an industrial process, or an ingredient in a diagnostic reagent. Examples of heterologous proteins of interest compatible with the systems provided herein include antibodies and antigen binding fragments thereof, antibody fusions, Fc domain fusions, cytokines, cytokine receptors, signaling proteins, enzymes, viral proteins, cancer antigens, peptide hormones, fusion proteins of any of these, and variants of any of these. In some embodiments, the heterologous protein of interest is a mammalian protein or a derivative thereof. In some embodiments, the heterologous protein of interest is a human protein or a derivative thereof.

Also provided herein are selection systems for heterologous protein expression in the cells provide herein. In some embodiments, the selection system comprises a cell as provided herein (e.g., a non-naturally occurring mammalian cell comprising an inoperative genomic asparaginase (Aspg) gene and an inoperative glutamine synthetase (Gs) gene, and wherein the cell further comprises one or more vectors (e.g., plasmids) encoding a controllably expressed Aspg gene, a controllably expressed Gs gene, and a controllably expressed gene encoding a heterologous protein of interest) and a selection medium.

In some embodiments, the selection medium is one in which cells (e.g., double knockout cells as provided herein) which do not comprise the one or more vectors encoding the controllably expressed Aspg gene and/or the controllably expressed Gs gene die or otherwise fail to propagate but in which cells which do comprise the one or more vectors survive and/or propagate (e.g., propagate at a greater rate than the cells without the one or more vectors). In some embodiments, the selection medium is a medium which contains substantially no glutamine. In some embodiments, the selection medium contains only trace amounts of glutamine. In some embodiments, the selection medium comprises at most about 1 mM glutamine, at most about 0.1 mM glutamine, at most about 0.01 mM glutamine, or at most about 0.001 mM glutamine. In some embodiments, the cells are transferred to a medium which contains no detectable glutamine for the selection step, though traces of glutamine may be present upon transfer of the cells into the selection medium as carryover (e.g., glutamine is transferred to the selection medium with the cells themselves, occurs in trace amounts from breakdown of excreted proteins, or traces of old media from pre-selection culture containing glutamine is carried over).

In some embodiments, gene knockout and/or transfection (as well as culturing in between gene knockout and transfection) occurs in a medium which is capable of sustaining the cells which have had the Gs and Aspg genes knocked out. In some embodiments, this medium comprises supplemental glutamine which allows the cells with Gs and Aspg knockout to continue to survive and propagate. In some embodiments, this medium comprises at least about 4 mM glutamine, at least about 5 mM glutamine, at least about 6 mM glutamine, at least about 7 mM glutamine, or at least about 8 mM glutamine. In some embodiments, it is necessary to sustain the level of glutamine above a certain threshold amount prior to transfer of the cells to the selection medium. In some embodiments, maintaining the threshold amount of glutamine comprises regularly replenishing media to keep the glutamine level above the threshold amount and/or regularly supplementing the medium with glutamine.

In some embodiments, the selection medium comprises additional supplements which facilitate or enhance the selection process or otherwise increase expression of the heterologous protein of interest. In some embodiments, the selection medium further comprises 1, 2, 3, 4, 5, 6, 7, 8, 9, 10 or 11 supplements selected from L-alanine, L-asparagine, L-aspartic acid, L-glutamic acid, L-proline, L-serine, adenosine, guanosine, cytidine, uridine, and thymidine. In some embodiments, the selection media is supplemented with a glutamine synthetase selection medium (GSEM) supplement. GSEM supplement is a supplement comprising L-alanine, L-asparagine, L-aspartic acid, L-glutamic acid, L-proline, L-serine, adenosine, guanosine, cytidine, uridine, and/or thymidine. Commercially available GSEM supplements are sold by Millipore Sigma (e.g., product number G9785) as a 50× concentrate which contains (mg/L): L-alanine 450.0, L-asparagine*$H_2O$ 4261.0, L-aspartic acid 650.0, L-glutamic acid 3750.0, L-proline 575.0, L-serine 500.0, adenosine 350.0, guanosine 350.0, cytidine 350.0, uridine 350.0, and thymidine 12.0. In some embodiments, GSEM supplemented medium is a medium which contains about 5-15 mg/L L-alanine, about 70-100 mg/L L-asparagine*$H_2O$, about 10-20 mg/L L-aspartic acid, about 80-120 mg/L L-glutamic acid, about 5-15 mg/L L-proline, about 5-15 mg/L L-serine, about 5-10 mg/L adenosine, about 5-10 mg/L guanosine, about 5-10 mg/L cytidine, about 5-10 mg/L uridine, and about 0.15-0.35 mg/L thymidine. In some embodiments, the GSEM supplemented medium contains about 9 mg/L L-alanine, about 85 mg/L L-asparagine*$H_2O$, about 13 mg/L L-aspartic acid, about 95 mg/L L-glutamic acid, about 11.5 mg/L L-proline, about 10 mg/L L-serine, about 9 mg/L adenosine, about 7 mg/L guanosine, about 7 mg/L cytidine, about 7 mg/L uridine, and about 0.24 mg/L thymidine.

In another aspect provided herein is a method of expressing a heterologous protein of interest in a cell provided herein. The heterologous protein of interest can be any of the examples provided herein, or any other desired heterologous protein. In some embodiments, expressing the heterologous protein of interest comprises culturing the cell under conditions which are optimized to produce the desired heterologous protein in high yield and in high quality. Such expression can occur at any desired scale or size desired, including in industrial sizes at scales of 100s or 1000s of liters or more. In some embodiments, culture conditions are optimized to give a high yield of the desired protein from the cells provided herein. Examples of parameters that can be further optimized to improve yield of a heterologous protein of interest expressed from cells and systems provided herein include culture times, culture temperature, dissolved gas content (e.g., dissolved $CO_2$ or dissolved oxygen), culture pH, and the like, as well as through optimization of downstream processing of the protein of interest (e.g., purification and formulation). Techniques for process optimization are well known in the art and generally compatible with the cells and systems provided herein.

In another aspect provided herein is a heterologous protein expressed by a cell as provided herein. In another aspect is a pharmaceutical composition comprising a heterologous protein expressed by a cell as provided herein and a pharmaceutically acceptable carrier.

In another aspect is a method of preparing a non-naturally occurring mammalian cell for the production of a heterologous protein of interest. In some embodiments, the method comprises creating a mammalian cell which comprises knockouts of an asparaginase (Aspg) gene and a glutamine synthetase (Gs) gene. In some embodiments, the preparing the gene knockouts comprises contacting the mammalian cell with a gene editing system configured to inactivate an asparaginase (Aspg) gene and a glutamine synthetase (Gs) gene. The gene editing system can be any of the gene editing systems provided herein or otherwise known in the art. In some embodiments, preparing the knockout comprises knocking out each allele of the relevant gene such that the cell is completely unable to express the encoded genes without an exogenous vector.

In some embodiments, the knockout cell line can be transfected with one or more plasmids shorty after creating the knockout or the knockout cell line can be used to create a cell bank which can be transfected at a later date. In some embodiments, creating the cell bank comprises propagating the knockout cells (optionally after a selection step) to produce a large population of cells. This population of cells will include descendent cells of the original cell which also contain the gene knockouts and which are also amenable to the expression of heterologous proteins as provided herein. This large population of cells can then be split and banked (e.g., aliquoted and frozen) until a later date. One aspect of the invention provided herein is a cell comprising the knockout genes (e.g., Gs and Aspg) which can then be used to express the heterologous proteins using the plasmid systems provided herein. Another aspect of the invention provided herein is a cell bank of the cells comprising the knockout genes (e.g., Gs and Aspg) provided herein.

In some embodiments, the method of preparing the non-naturally occurring mammalian cell line comprises transfecting the mammalian cell with the gene knockouts or a descendent cell with the gene knockouts with a controllably expressed Aspg gene, a controllable expressed Gs gene, and a controllably expressed gene encoding the heterologous protein of interest. In some embodiments, the controllably expressed Aspg gene is present on a vector (e.g., a plasmid) which also comprises the controllably expressed gene encoding the heterologous protein of interest. In some embodiments, the controllably expressed Gs gene is present on a vector (e.g., a plasmid) which also comprises the controllably expressed gene encoding the heterologous protein of interest. In some embodiments, both the vector comprising the controllably expressed Aspg gene and the vector comprising the controllably expressed Gs gene comprise copies of the controllably expressed gene encoding the heterologous protein of interest.

In some embodiments, the method of preparing the non-naturally occurring mammalian cell line comprises transfecting the mammalian cell or a descendent of the mammalian cell with i) a first plasmid comprising a controllably expressed Aspg gene and a first controllably expressed gene encoding the heterologous protein of interest; and ii) a second plasmid comprising a controllably expressed Gs gene and a second controllably expressed gene encoding the heterologous protein of interest. In some embodiments, the two plasmids are transfected at the same time. In some embodiments, the two plasmids are transfected under conditions such that most cells (e.g., at least 50%, at least 60%, at least 70%, at least 80%, or at least 90%) of a cell culture will receive at least one copy of each of the two plasmids.

In some embodiments, the method of preparing the non-naturally occurring mammalian cell line further comprises placing the transfected mammalian cell into a selection medium. In some embodiments, the selection medium is one as provided herein. In some embodiments, the selection medium contains substantially no glutamine.

Surprisingly, the cells, systems, and methods provided herein for expressing a heterologous protein of interest provide for enhanced expression of the protein of interest compared to other methods, particularly as compared to cells, systems, and methods which involve the knockout of only a single gene (e.g., a cell which has only the Gs gene knocked out). In some embodiments, a cell or cell culture containing a Gs knockout, a Aspg knockout, and plasmids controllably expressing the Gs gene and the Aspg gene on separate plasmids which also controllably express the heterologous protein of interest display enhanced specific productivity compared to a corresponding cell or cell culture which comprises only the Gs knockout and a plasmid comprising a controllably expressed Gs gene and a controllably expressed gene encoding the heterologous protein of interest. In some embodiments, the specific productivity of the double knockout cell line is enhanced by at least 1.5-fold, at least 2-fold, at least 2.5-fold, at least 3-fold, at least 4-fold, at least 5-fold, at least 6-fold, at least 7-fold, at least 8-fold, at least 9-fold, at least 10-fold, at least 11-fold, at least 12-fold, at least 13-fold, at least 14-fold, or at least 15-fold compared to the Gs knockout only. In some embodiments, the comparison is made in the initial transfection culture. In some embodiments, the comparison is made after further adaptation to a different culture format (e.g., 1 week, 2 week, 3 week, 4 week, 5 week, 6 week, or longer adaptation to a suspension culture format where the initial transfection was in an adherent format).

In some embodiments, the double knockout cells (Gs and Aspg knockouts) which comprise two transfected plasmids controllably expressing the Gs and Asp genes produce a higher titer of heterologous protein of interest when compared to corresponding cells which contain only the Gs knockout and plasmid controllably expressing the Gs gene. In some embodiments, heterologous protein titer of the double knockout cells is enhanced by at least 1.5 fold, at least 2-fold, at least 3-fold, at least 4-fold, or at least 5-fold compared to the Gs only knockout. In some embodiments, the comparison is made in the initial transfection culture. In some embodiments, the comparison is made after further adaptation to a different culture format (e.g., 1 week, 2 week, 3 week, 4 week, 5 week, 6 week, or longer adaptation to a suspension culture format where the initial transfection was in an adherent format).

In some embodiments, the double knockout cells display enhanced specific productivity after transfection compared to single knockout cells, yet display lower total levels of heterologous protein production (e.g., owing to lower cell count or viable cell counts after transfection). In such instances, the total heterologous protein production may sometime be improved through further adaptation of the cell line which results in increased cell counts, viable cell counts, and/or growth of the cells. Such adaptation can be performed using many methods known in the art to enhance the health and viability of cells in culture.

All publications, patents, and patent applications mentioned in this specification are herein incorporated by reference to the same extent as if each individual publication, patent, or patent application was specifically and individually indicated to be incorporated by reference.

Unless defined otherwise, all technical and scientific terms and any acronyms used herein have the same meanings as commonly understood by one of ordinary skill in the art in the field of the invention. Although any methods and materials similar or equivalent to those described herein can be used in the practice of the present invention, the exemplary methods, devices, and materials are described herein.

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, $2^{nd}$ ed. (Sambrook et al., 1989); Oligonucleotide Synthesis (M. J. Gait, ed., 1984); Animal Cell Culture (R. I. Freshney, ed., 1987); Methods in Enzymology (Academic Press, Inc.); Current Protocols in Molecular Biology (F. M. Ausubel et al., eds., 1987, and periodic updates); PCR: The Polymerase Chain Reaction (Mullis et al., eds., 1994); Remington, The Science and Practice of Pharmacy, $20^{th}$ ed., (Lippincott, Williams & Wilkins 2003), and Remington, The Science and Practice of Pharmacy, $22^{th}$ ed., (Pharmaceutical Press and Philadelphia College of Pharmacy at University of the Sciences 2012).

Definitions

As used herein, the terms "comprises," "comprising," "includes," "including," "has," "having," "contains", "containing," "characterized by," or any other variation thereof, are intended to encompass a non-exclusive inclusion, subject to any limitation explicitly indicated otherwise, of the recited components. For example, a fusion protein, a pharmaceutical composition, and/or a method that "comprises" a list of elements (e.g., components, features, or steps) is not necessarily limited to only those elements (or components or steps), but may include other elements (or components or steps) not expressly listed or inherent to the fusion protein, pharmaceutical composition and/or method.

As used herein, the transitional phrases "consists of" and "consisting of" exclude any element, step, or component not specified. For example, "consists of" or "consisting of" used in a claim would limit the claim to the components, materials or steps specifically recited in the claim except for impurities ordinarily associated therewith (i.e., impurities within a given component). When the phrase "consists of" or "consisting of" appears in a clause of the body of a claim, rather than immediately following the preamble, the phrase "consists of" or "consisting of" limits only the elements (or components or steps) set forth in that clause; other elements (or components) are not excluded from the claim as a whole.

As used herein, the transitional phrases "consists essentially of" and "consisting essentially of" are used to define a fusion protein, pharmaceutical composition, and/or method that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

The term "and/or" when used in a list of two or more items, means that any one of the listed items can be employed by itself or in combination with any one or more of the listed items. For example, the expression "A and/or B" is intended to mean either or both of A and B, i.e. A alone, B alone or A and B in combination. The expression "A, B and/or C" is intended to mean A alone, B alone, C alone, A and B in combination, A and C in combination, B and C in combination or A, B, and C in combination.

It is understood that aspects and embodiments of the invention described herein include "consisting" and/or "consisting essentially of" aspects and embodiments.

It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range. Values or ranges may be also be expressed herein as "about," from "about" one particular value, and/or to "about" another particular value. When such values or ranges are expressed, other embodiments disclosed include the specific value recited, from the one particular value, and/or to the other particular value. Similarly, when values are expressed as approximations, by use of the antecedent "about," it will be understood that the particular value forms another embodiment. It will be further understood that there are a number of values disclosed therein, and that each value is also herein disclosed as "about" that particular value in addition to the value itself. In embodiments, "about" can be used to mean, for example, within 10% of the recited value, within 5% of the recited value, or within 2% of the recited value.

As used herein, the term "specific productivity" refers to the amount of an indicated protein produced by an average cell in a culture over a given time. Specific productivity herein is typically given in units of pg/cell/day (unless otherwise specified) and is sometimes denoted $q_p$. Unless otherwise specified, specific productivity values provided herein are calculated over an entire culture duration (e.g., time from transfer of cell culture to new media until final measurement).

As used herein the term "pharmaceutically acceptable" means approved by a regulatory agency of the Federal or a state government or listed in the U.S. Pharmacopoeia, other generally recognized pharmacopoeia in addition to other formulations that are safe for use in animals, and more particularly in humans and/or non-human mammals.

As used herein the term "pharmaceutically acceptable carrier" refers to an excipient, diluent, preservative, solubilizer, emulsifier, adjuvant, and/or vehicle with which demethylation compound(s), is administered. Such carriers may be sterile liquids, such as water and oils, including those of petroleum, animal, vegetable or synthetic origin, such as peanut oil, soybean oil, mineral oil, sesame oil and the like, polyethylene glycols, glycerine, propylene glycol or other synthetic solvents. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose may also be a carrier. Methods for producing compositions in combination with carriers are known to those of skill in the art. In some embodiments, the language "pharmaceutically acceptable carrier" is intended to include any and all solvents, dispersion media, coatings, isotonic and absorption delaying agents, and the like, compatible with pharmaceutical administration. The use of such media and agents for pharmaceutically active substances is well known in the art. See, e.g., Remington, The Science and Practice of Pharmacy, 20th ed., (Lippincott, Williams & Wilkins 2003). Except insofar as any conventional media or agent is incompatible with the active compound, such use in the compositions is contemplated.

"Polymerase chain reaction" (PCR) generally refers to a process that uses multiple cycles of nucleic acid denaturation, annealing of primer pairs to opposite strands (forward and reverse), and primer extension to exponentially increase copy numbers of a target nucleic acid sequence. In a variation called RT-PCR, reverse transcriptase (RT) is used to make a complementary DNA (cDNA) from mRNA, and the cDNA is then amplified by PCR to produce multiple copies of DNA. There are many permutations of PCR known to those of ordinary skill in the art.

A "sequence" of a nucleic acid refers to the order and identity of nucleotides in the nucleic acid. A sequence is typically read in the 5' to 3' direction. The terms "identical" or percent "identity" in the context of two or more nucleic acid or polypeptide sequences, refer to two or more sequences or subsequences that are the same or have a specified percentage of amino acid residues or nucleotides that are the same, when compared and aligned for maximum correspondence, e.g., as measured using one of the sequence comparison algorithms available to persons of skill or by visual inspection.

In some embodiments, the Cas protein or the variant thereof is a Cas9 protein or a variant thereof. Isolated Cas9-crRNA complex from the *S. thermophilus* CRISPR-Cas system as well as complex assembled in vitro from separate components demonstrate that it binds to both synthetic oligodeoxynucleotide and plasmid DNA bearing a nucleotide sequence complementary to the crRNA. It has been shown that Cas9 has two nuclease domains—RuvC— and HNH-active sites/nuclease domains, and these two nuclease domains are responsible for the cleavage of opposite DNA strands. In some embodiments, the Cas9 protein is derived from Cas9 protein of *S. thermophilus* CRISPR-Cas system. In some embodiments, the Cas9 protein is a multidomain protein having about 1,409 amino acids residues.

It should be appreciated that any CRISPR-Cas systems capable of disrupting the double stranded nucleic acid and creating a loop structure can be used in the present methods. For example, the Cas proteins provided herein may include, but not limited to, the Cas proteins described in Haft et al., *PLoS Comput Biol.*, 2005, 1(6): e60, and Zhang et al., *Nucl. Acids Res.*, 2013, 10.1093/nar/gkt1262. Some of these CRISPR-Cas systems require that a specific sequence be present for these CRISPR-Cas systems to recognize and bind to the target sequence. For instance, Cas9 may require the presence of a 5'-NGG protospacer-adjacent motif (PAM). Thus, in some embodiments, a PAM sequence or a sequence complementary to a PAM sequence is engineered into the target nucleic acid for initiating the binding of the CRISPR-Cas systems to the target nucleic acid.

As used herein, the term "guide polynucleotide" (e.g., a guide RNA), refers to a polynucleotide sequence that can form a complex with an endonuclease (e.g., Cas protein such as Cas9) and enables the endonuclease to recognize and optionally cleave a target site on a polynucleotide such as DNA. The guide polynucleotide can be a single molecule or a double molecule. The guide polynucleotide sequence can be a RNA sequence, a DNA sequence, or a combination thereof (a RNA-DNA combination sequence). Optionally, the guide polynucleotide can comprise at least one nucleotide, phosphodiester bond, or linkage modification such as, but not limited to, locked nucleic acid (LNA), peptide nucleic acid (PNA), bridged nucleic acid (BNA), 5-methyl dC, 2,6-Diaminopurine, 2'-Fluoro A, 2'-Fluoro U, 2'-O-Methyl RNA, Phosphorothioate bond, linkage to a cholesterol molecule, linkage to a polyethylene glycol molecule, linkage to a spacer 18 (hexaethylene glycol chain) molecule, or 5' to 3' covalent linkage resulting in circularization. In some embodiments, the guide polynucleotide does not solely comprise ribonucleic acids (RNAs). In other embodiments, the guide polynucleotide does solely comprise ribonucleic acids (RNAs). A guide polynucleotide that solely comprises ribonucleic acids is also referred to as a "guide RNA".

In general, a guide polynucleotide is any polynucleotide sequence having sufficient complementarity with a target polynucleotide sequence to hybridize with the target sequence and direct sequence-specific binding of a CRISPR complex to the target sequence. In some embodiments, the degree of complementarity between a guide polynucleotide and its corresponding target sequence, when optimally aligned using a suitable alignment algorithm, is about or at least about 50%, 55%, 60%, 65%, 70%, 75%, 80%, 85%, 90%, 95%, 96%, 97%, 98%, 99%, 99.5%, 99.9%, or 100%. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g., the Burrows Wheeler Aligner), Clustal W, Clustal X, BLAT, Novoalign (Novocraft Technologies, ELAND (Illumina, San Diego, Calif.), SOAP (available at soap.genomics.org.cn), and Maq (available at maq.sourceforge.net).

EXAMPLES

The dominant method for generating Chinese hamster ovary (CHO) cell lines that produce high titers of biotherapeutic proteins utilizes selection methods such as dihydrofolate reductase (Dhfr) or glutamine synthetase (Gs), alongside inhibitory compounds like methotrexate (MTX) or methionine sulfoximine (MSX), respectively. Recent work has shown the importance of asparaginase (Aspg) for growth in media lacking glutamine—the selection medium for Gs-based selection systems. In this example, a Gs/Aspg double knockout CHO cell line was developed and evaluated for its utility as a novel dual selectable system via co-transfection of Gs-Enbrel and Aspg-Enbrel plasmids. Using the same selection conditions as the standard Gs system, the resulting cells from the Gs/Aspg dual selection showed substantially improved specific productivity and titer compared to the standard Gs selection method, however, with reduced growth rate and viability. Following adaptation in selection medium, the cells improved viability and growth while still achieving ~5× higher specific productivity and ~3× higher titer than Gs selection alone. Further optimization of culture medium and selection conditions using this approach could serve as an effective addition to workflows for the industrial production of recombinant biotherapeutics.

To confirm the importance of Aspg for growth in glutamine-free media and assess its viability for use as an additional selectable marker simultaneously with Gs, three clonal knockout (KO) cell lines were generated using CRISPR/Cas9: Gs–KO, Aspg–KO, and Gs/Aspg–KO. Knockouts had verified frameshift insertions or deletions in all alleles and also showed decreased mRNA expression.

Both clones lacking Aspg showed decreased maximum viable cell density when grown in a glutamine-containing medium but with comparable growth rates to the Gs KO line. When grown without glutamine, Aspg knockout cells showed negligible growth, but remained viable. Gs/Aspg-KO cells, on the other hand, showed a dramatic decrease in cell viability—even more quickly than Gs-KO cells. This suggested that a double selection system using Gs and Aspg simultaneously would be more stringent than Gs alone—while still using only glutamine deprivation as the sole selective pressure.

Figure 7A:
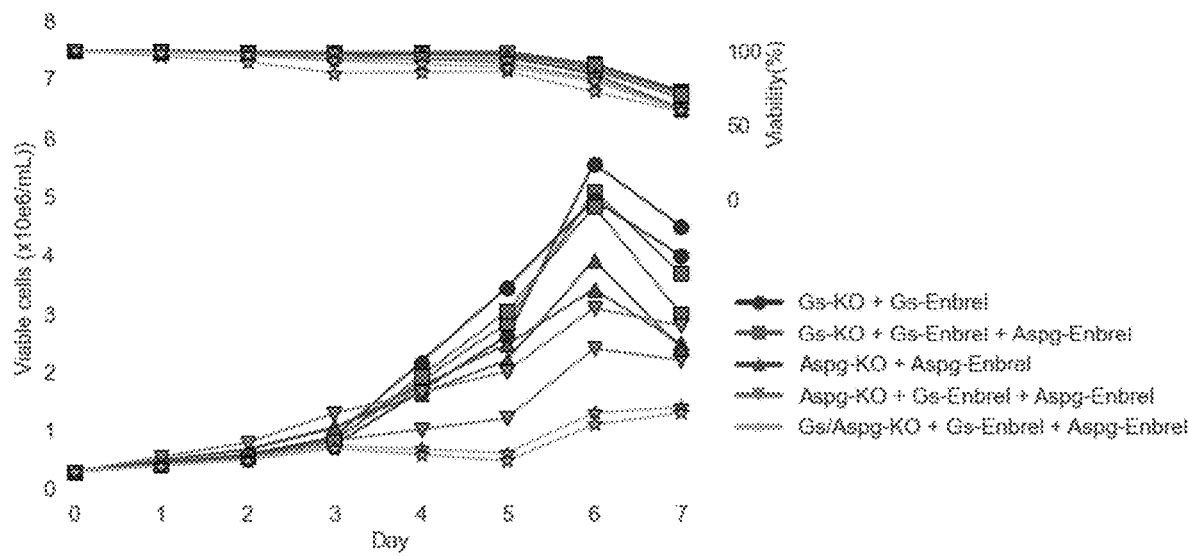
FIG. 7A shows viable cell density and viability in a batch culture of bulk selected pools grown in medium without glutamine.
Figure 7B:
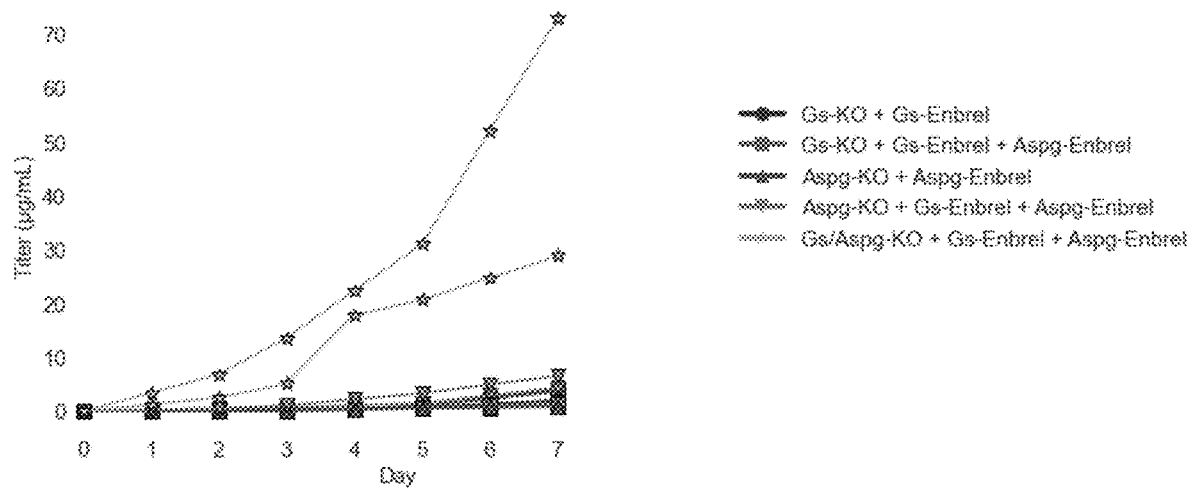
FIG. 7B shows titer in a batch culture of bulk selected pools grown in medium without glutamine.

Enbrel-producing cells were generated from the different knockout lines via 5 different transfections: 1) GS-KO cells with a Gs+Enbrel plasmid, 2) GS-KO cells with both Gs+Enbrel and Aspg+Enbrel plasmids, 3) Aspg-KO cells with Aspg+Enbrel plasmid, 4) Aspg-KO cells with both Gs+Enbrel and Aspg+Enbrel plasmids, and 5) double Gs/Aspg-KO cells with both Gs+Enbrel and Aspg+Enbrel plasmids, and subjected to the workflow depicted in FIG. 1. Selection in both static minipools (192/transfection) and bulk suspension format (duplicates in 6 well suspension, permitting quantification of recovery profiles) was tested. Following recovery, surviving minipools were split 1:2 and evaluated for terminal cell count and titer. After 5 days of culture, minipools derived from clones with Aspg knockouts showed lower cell density (viable cell density (VCD) shown in FIG. 2A) and product titer (FIG. 2B); however, minipools derived from the Gs/Aspg double knockout transfected with both plasmids showed ~3-4× higher median cell-normalized product titer than Gs knockout derived minipools (FIG. 2C, Table 1 below). No change in recovery timelines in the bulk suspension format was observed. After characterization of recovered pools in batch culture, the Gs/Aspg double knockout cells transfected with both plasmids again showed depressed growth (FIG. 7A), but significantly (~16×) higher titer and specific productivity (FIG. 7B).

TABLE 1

Figure 2A:
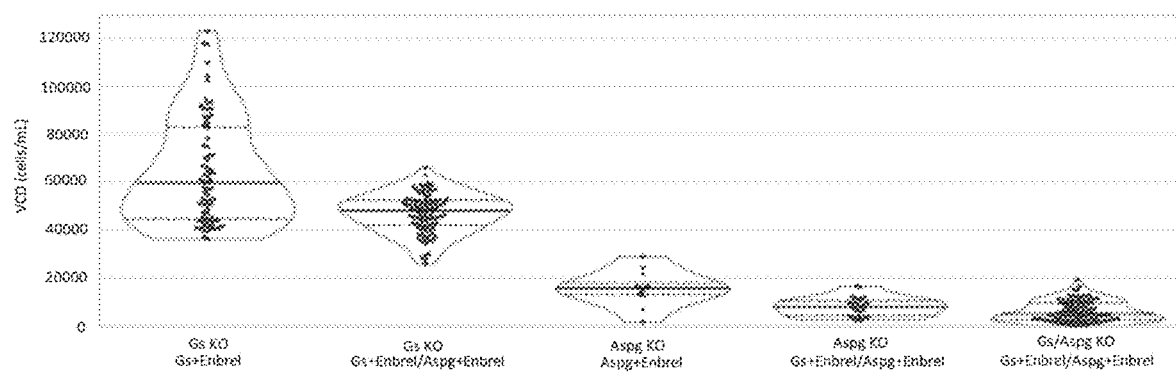
FIG. 2A shows viable cell density (VCD) from minipool results from 96 well plates after 5 days of culture. In each of FIGS. 2A-2C, Red dashed lines indicate 1st and 3rd quartiles and black solid lines indicate medians. While the viable cell density of the Gs/Aspg double KO was much initially lower, the amount of protein produced per cell in minipools were substantially higher for the mutant.
Figure 2B:
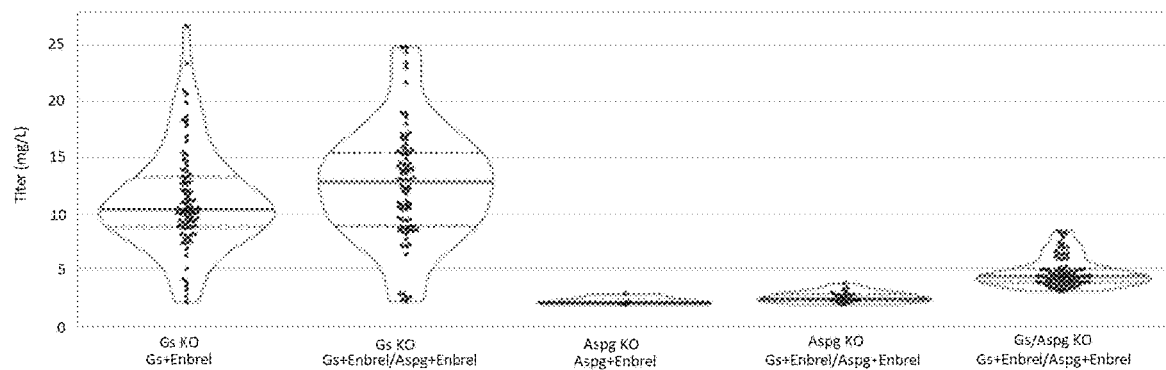
FIG. 2B shows titer from minipool results from 96 well plates after 5 days of culture.
Figure 2C:
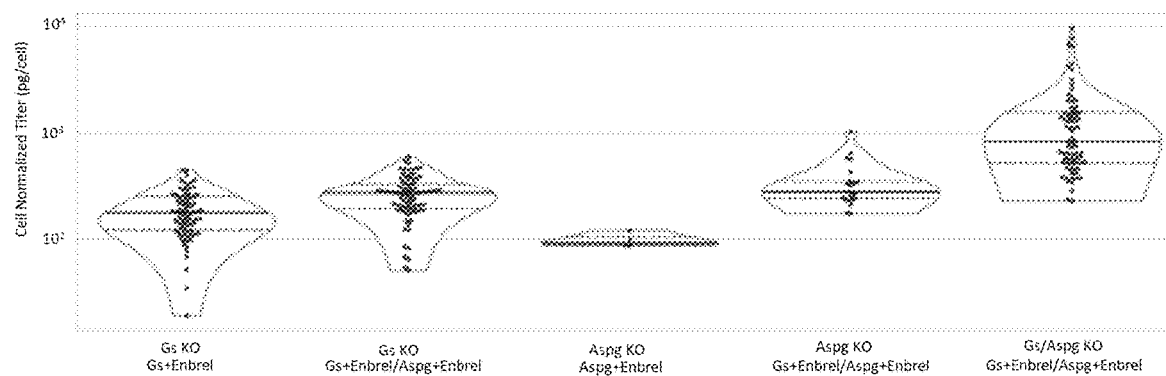
FIG. 2C shows cell normalized titer from minipool results from 96 well plates after 5 days of culture.

96 well results from FIGS. 2A-2C

| | VCD (×10⁴ cells/mL) | Titer (mg/L) | Cell-Normalized Titer (pg/cell) |
|---|---|---|---|
| Gs KO Gs-Enbrel | Q1: 4.48 Median: 5.99 Q3: 8.29 | Q1: 8.72 Median: 10.26 Q3: 13.23 | Q1: 119.1 Median: 176.5 Q3: 251.5 |
| Gs KO Gs-Enbrel Aspg-Enbrel | Q1: 4.18 Median: 4.80 Q3: 5.24 | Q1: 8.79 Median: 12.67 Q3: 15.39 | Q1: 191.1 Median: 272.1 Q3: 337.3 |
| Aspg KO Aspg-Enbrel | Q1: 1.33 Median: 1.60 Q3: 1.80 | Q1: 1.97 Median: 2.05 Q3: 2.29 | Q1: 86.5 Median: 92.1 Q3: 103.0 |
| Aspg KO Gs-Enbrel Aspg-Enbrel | Q1: 0.43 Median: 0.83 Q3: 1.06 | Q1: 2.21 Median: 2.43 Q3: 2.77 | Q1: 239.0 Median: 278.9 Q3: 356.3 |
| Gs/Aspg KO Gs-Enbrel Aspg-Enbrel | Q1: 0.27 Median: 0.50 Q3: 0.96 | Q1: 3.84 Median: 4.39 Q3: 5.04 | Q1: 530.7 Median: 839.1 Q3: 1564.9 |

It was then tested if minipools could obtain improved performance after being transitioned to suspension culture. Top minipools from all transfections were expanded and characterized in 6 well suspension culture. The trend of higher titer and specific productivity in Gs/Aspg double knockout derived minipools was maintained, but minipools derived from cells with Aspg knocked out showed decreased viability. The top 3 Gs/Aspg knockout derived and Gs knockout derived minipools (based on titer) were then expanded further to test if prolonged time in suspension culture would improve the performance of the former.

After expansion in shake flask culture, the growth and viability of Gs/Aspg double knockout derived minipools were still decreased compared to minipools derived from Gs knockout cells (FIG. 3A), but both were improved compared to their performance in 6-well plates. Significantly higher production of Enbrel was observed, both in titer (2-4× higher in the best performing Gs/Aspg-KO derived minipool) and specific productivity (10-15× improvement in Gs/Aspg-KO derived minipools) (FIG. 3B, Table 2 below).

TABLE 2

Figure 3A:
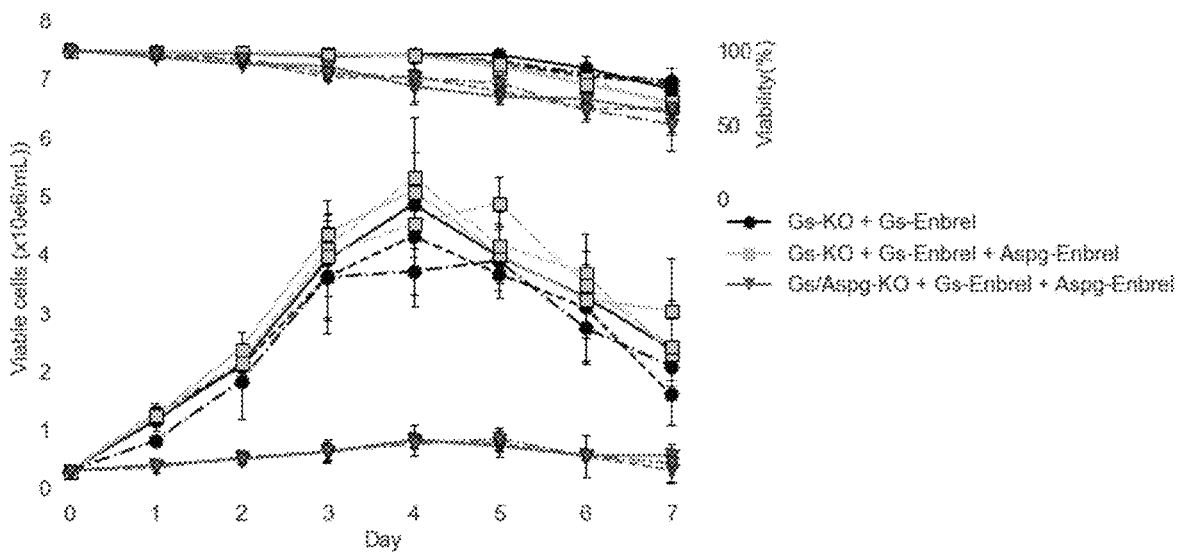
FIG. 3A shows viable cell density and viability in shake flask batch culture of top-producing minipools. For FIG. 3A and FIG. 3B, all cell line conditions are grown in three replicates; error bars represent standard deviation.
Figure 3B:
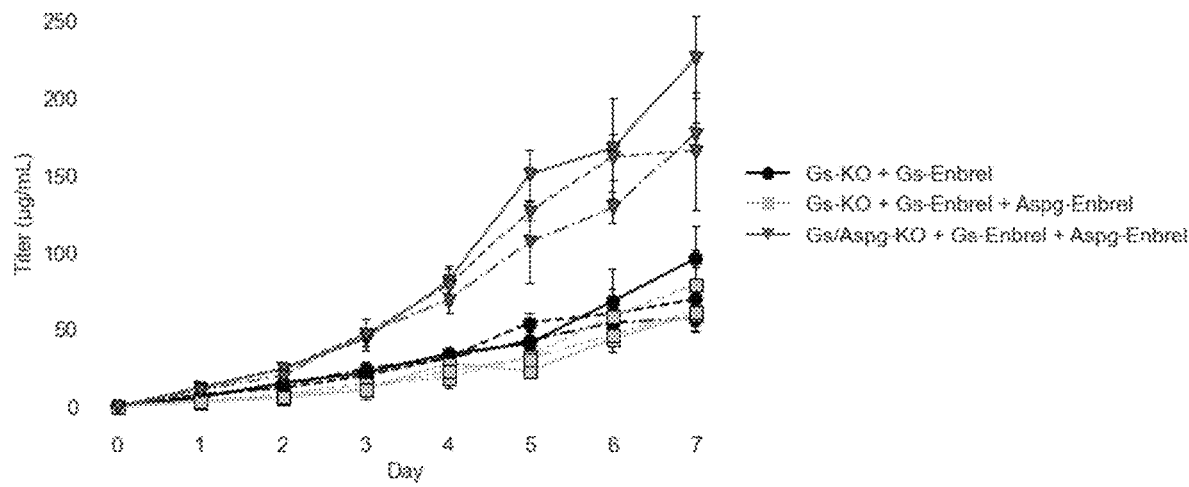
FIG. 3B shows titer in shake flask batch culture of top-producing minipools.

Flask results from FIGS. 3A and 3B

| | IVCC (×10⁶ cell day/mL) | $q_P$ (pg/cell/day) | Max Titer (mg/L) | Max VCD (×10⁶ cell/mL) |
|---|---|---|---|---|
| Gs KO Gs-Enbrel | 19.2 ± 1.6 | 3.52 ± 0.72 | 76.1 ± 22.0 | 4.58 ± 0.57 |
| Gs KO Gs-Enbrel Aspg-Enbrel | 21.9 ± 1.9 | 2.77 ± 0.69 | 67.3 ± 15.2 | 5.20 ± 0.67 |
| Gs/Aspg KO Gs-Enbrel Aspg-Enbrel | 4.0 ± 0.2 | 47.28 ± 8.74 | 194.3 ± 30.6 | 0.90 ± 0.12 |

IVCC = integral viable cell concentration

Figure 4:
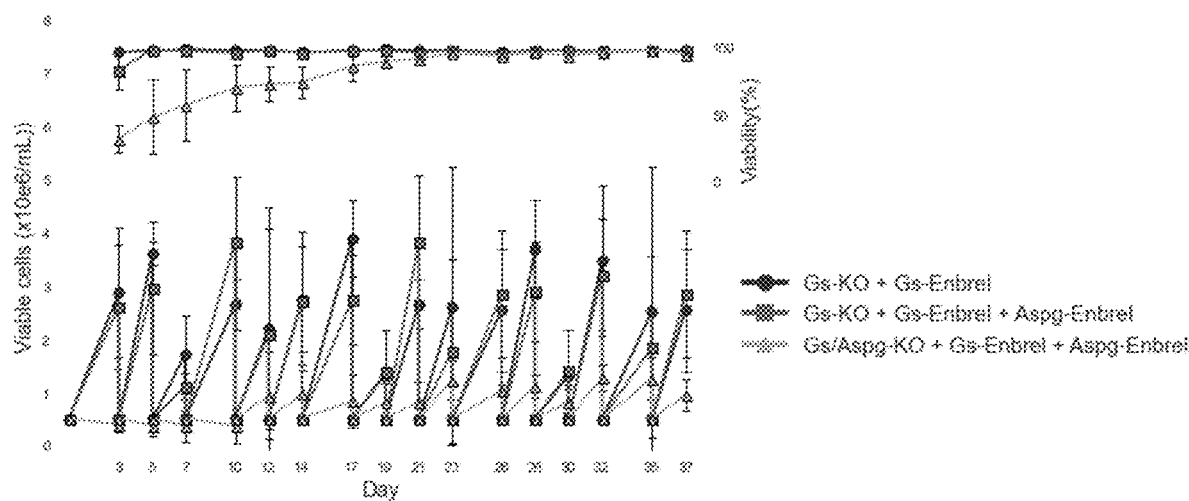
FIG. 4 shows cell growth and viability during prolonged adaptation to selection media (CD CHO w/out glutamine) for top minipools.

The improvement in growth and viability from 6-well to shake flask inspired further adaptation of minipools derived from Gs/Aspg knockout cells to see if this would improve performance in selection conditions designed for Gs knockout derived cells. Following ~1 month of adaptation (see FIG. 4, which shows viability information during the adaptation), the top minipool from each transfection was evaluated: The Gs/Aspg KO derived minipool showed significant improvements in growth and viability (FIG. 5A) while still outperforming the Gs knockout derivatives in titer and specific productivity (FIG. 5B and Table 3).

TABLE 3

Figure 5A:
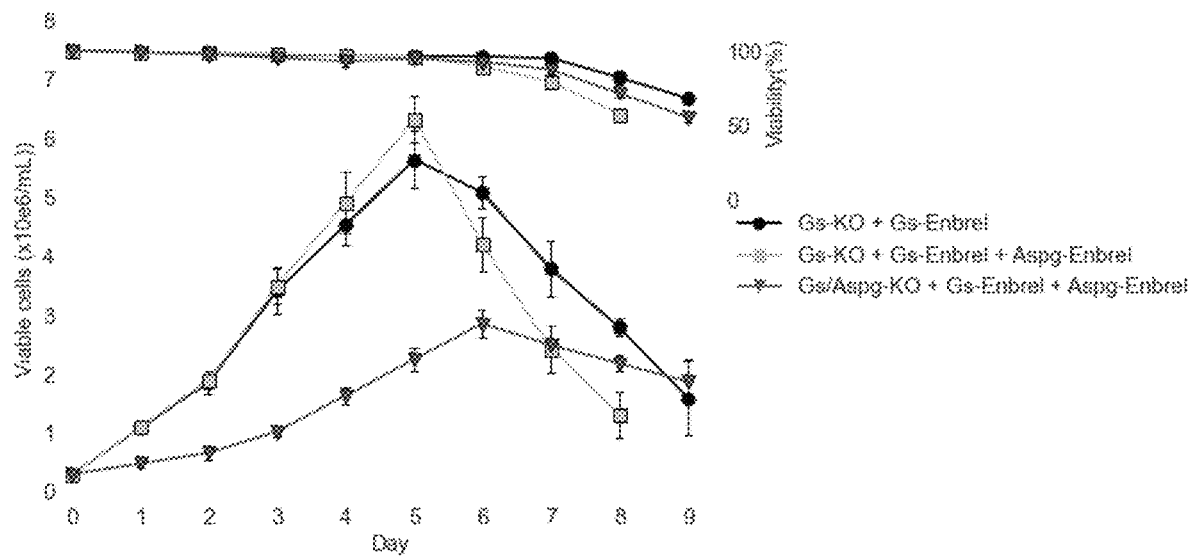
FIG. 5A shows viable cell density and viability in shake flask batch culture of the top minipool after adaptation.
Figure 5B:
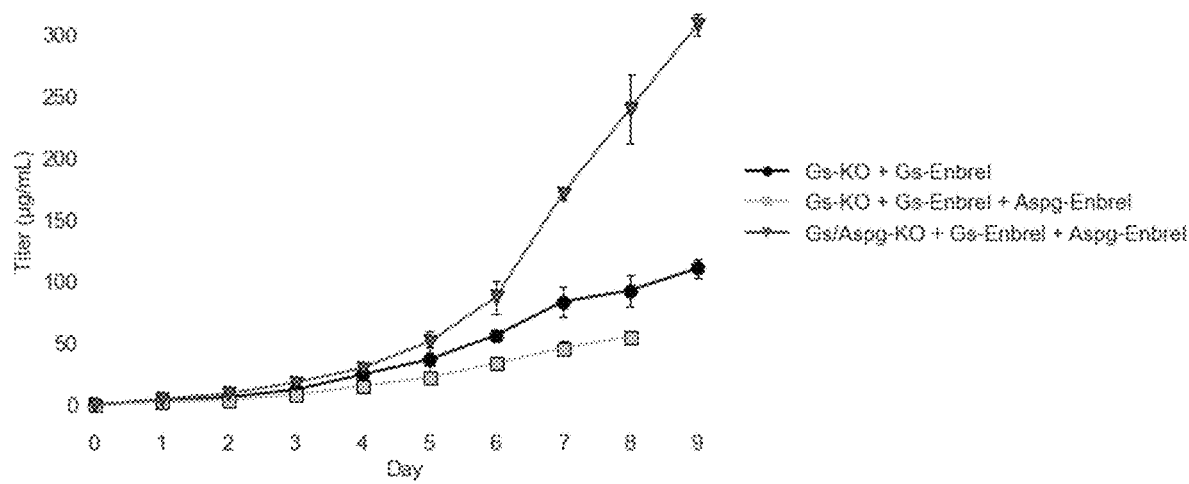

Batch culture with adapted cells (from FIGS. 5A and 5B). Specific productivity was calculated over the entire culture duration.

| | $q_P$ (pg/cell/day) | Max Titer (mg/L) | IVCC | Max VCD |
|---|---|---|---|---|
| Gs KO Gs-Enbrel | 3.60 ± 0.21 | 111.5 ± 5.5 | 29.1 ± 0.9 | 5.64 ± 0.48 |
| Gs KO Gs-Enbrel Aspg-Enbrel | 1.99 ± 0.11 | 55.0 ± 0.8 | 25.2 ± 0.9 | 6.32 ± 0.40 |
| Gs/Aspg KO Gs-Enbrel Aspg-Enbrel | 19.96 ± 0.53 | 308.0 ± 8.2 | 14.7 ± 0.5 | 2.86 ± 0.25 |

Figure 6A:
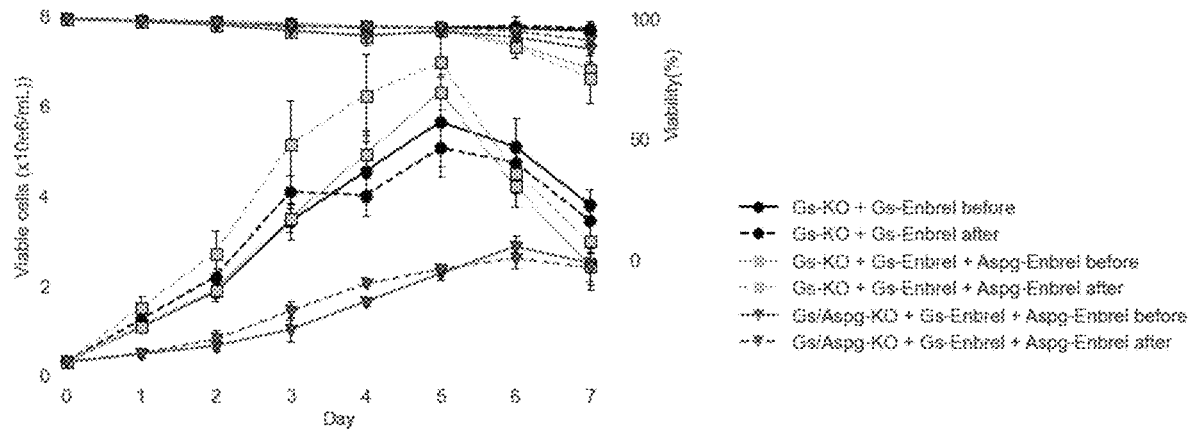
FIG. 6A shows viable cell density and viability in a batch culture which was performed before and after 4 weeks of culture to test the long-term stability of the indicated minipools. For FIG. 6A and FIG. 6B, all cell line conditions are grown in three replicates; error bars represent standard deviation.
Figure 6B:
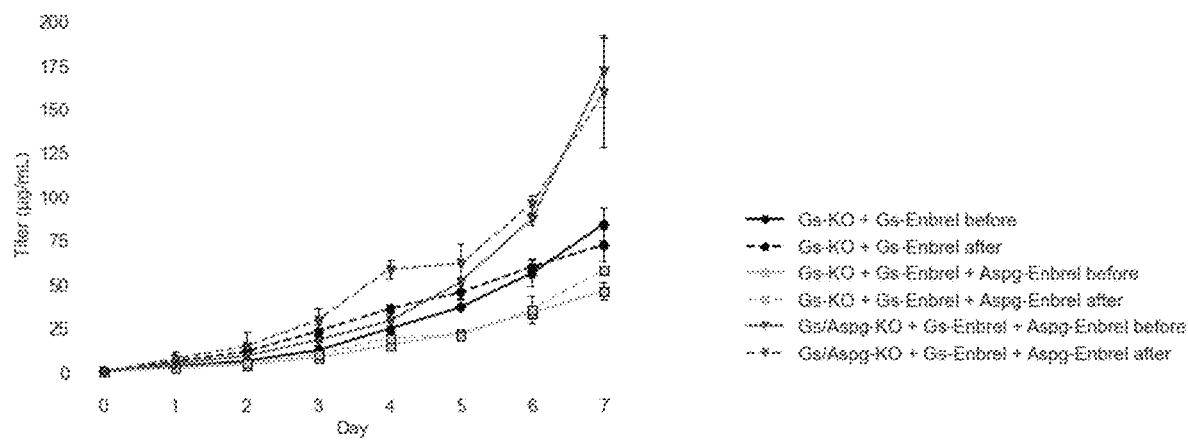
FIG. 6B shows titer in a batch culture which was performed before and after 4 weeks of culture to test the long-term stability of the indicated minipools.

The long-term stability of the dual selection strategy was further assessed and it was found that after an additional month of passaging, minipool performance remained stable. FIG. 6A shows viability and viable cell density for each minipool selection strategy evaluated, and FIG. 6B shows the corresponding titer. Numerical results of this experiment are shown in Table 4 below.

TABLE 4

Long term stability (from FIGS. 6A and 6B). Specific productivity was calculated over the entire culture duration.

| | $q_P$ (pg/cell/day) | Max Titer (mg/L) | Max VCD |
|---|---|---|---|
| Gs KO Gs-Enbrel | 3.31 ± 0.39 | 84.1 ± 9.2 | 5.64 ± 1.00 |
| Gs KO Gs-Enbrel-1 mo | 3.00 ± 0.38 | 72.2 ± 9.2 | 5.05 ± 0.64 |
| Gs KO Gs-Enbrel Aspg-Enbrel | 1.82 ± 0.2 | 46.0 ± 5.2 | 6.32 ± 0.40 |
| Gs KO Gs-Enbrel Aspg-Enbrel-1 mo | 1.70 ± 0.27 | 58.3 ± 2.1 | 6.97 ± 0.67 |
| Gs/Aspg KO Gs-Enbrel Aspg-Enbrel | 15.11 ± 1.31 | 171.7 ± 20.2 | 2.86 ± 0.25 |
| Gs/Aspg KO Gs-Enbrel Aspg-Enbrel-1 mo | 12.88 ± 2.30 | 159.3 ± 31.1 | 2.61 ± 0.22 |

Finally, the cause of poor growth in the Gs/Aspg–KO derived pools was explored. Cell growth in this selection system depends on the rescue of both knocked out enzymes (Gs and Aspg) through the uptake and integration of both transfected plasmids. It is possible that the observed low cell growth results from low expression of either or both plasmids after selection. However, both Gs and Aspg expression levels in the Gs/Aspg–KO derived pools were at least as high as that of Gs–KO derived pools following selection and recovery, prior to adaptation; thus, expression should be sufficient for robust growth. As adaptation partially recovered growth (and considerably improved viability) it is anticipated that additional media and/or platform optimization (e.g., altering the plasmid ratio) could further improve the performance of this system.

It was further investigated if the decreased growth of Aspg/Gs double knockout clones could be improved to obtain higher viable cell density. Thus, it was tested how the selection strategy works under a different set of conditions designed to improve recovery from the typical Gs selection process. Specifically, host cell lines were transfected in duplicate in 6 well plates (3,000,000 cells transfected/well) and conducted the selection in glutamine-free medium, either with or without glutamine synthetase expression medium (GSEM), a supplement typically used to facilitate cell recovery during glutamine selection. The selected pools were grown in batch culture in 6 well plates.

Figure 8:
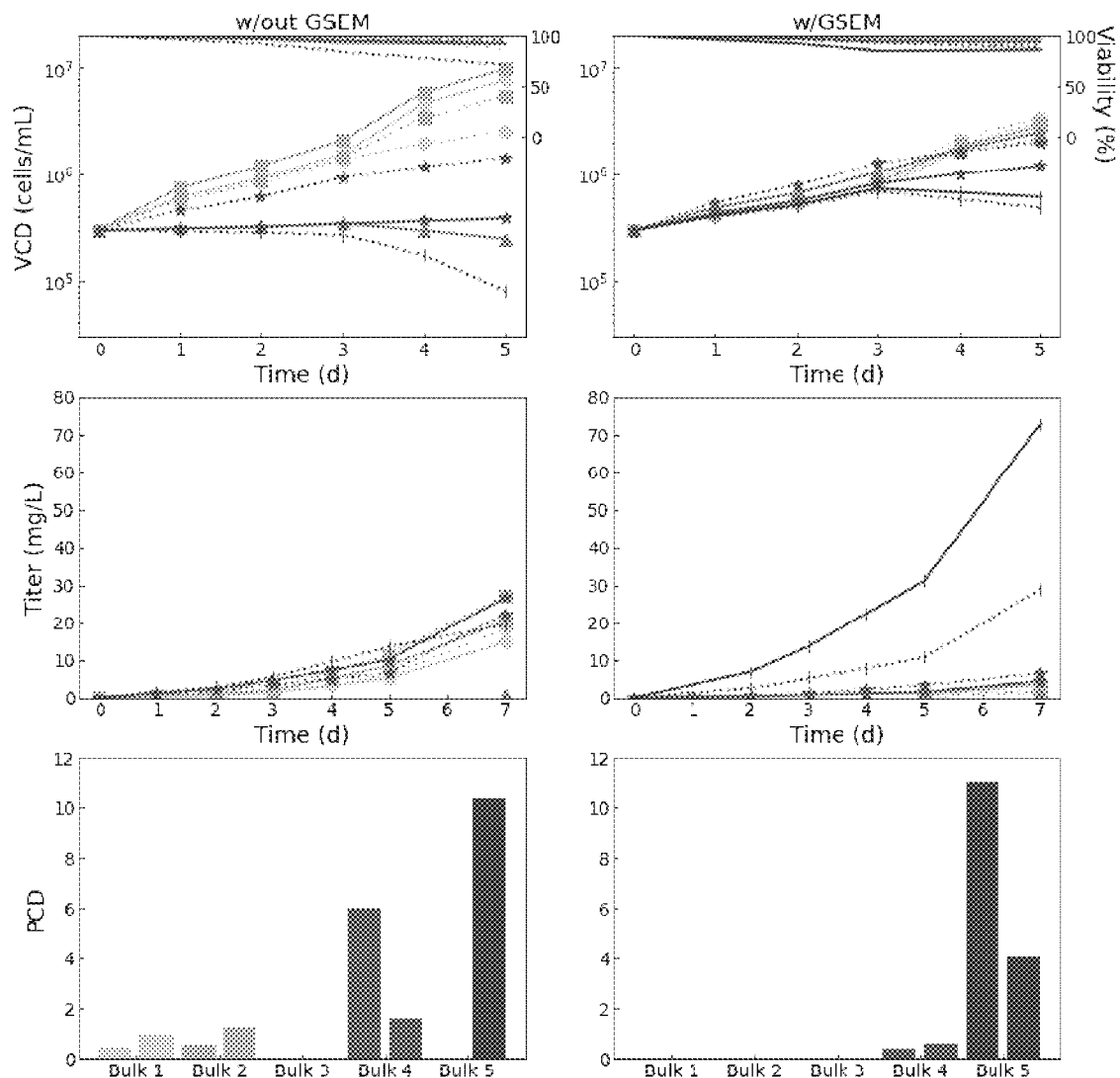
FIG. 8 shows VCD, titer and specific productivity measurements of bulk selection with and without glutamine synthetase expression medium. Different line styles represent replicates.

The Gs/Aspg KO transfected with both expression plasmids (Bulk 5) again exhibited a substantially greater specific productivity, both with and without GSEM. Interestingly, GSEM rescued growth of this cell line, indicating that media optimization and supplementation has the potential to improve cell behavior further. Specific productivity was calculated between days 0 and 5 (FIG. 8, Bulk 3 and Bulk 1-3 (without and with GSEM, respectively) did not produce detectable Enbrel until day 7 so specific productivity was not calculated). Bulk 4, the single Aspg KO cell line transfected with both plasmids, also displayed high specific productivity when selected without GSEM, but while the addition of GSEM improved the VCD, titer and specific productivity decreased. Thus, the optimal productivity is obtained in the Aspg/Gs KO, and selection using GSEM substantially improves the growth and titer of the cells. Further media optimization for the cell line could enable substantially improved growth of highly productive clones identified using this selection system.

The dual Gs/Aspg selection system thus is an intriguing option to generate more highly productive cell lines. As such it only requires a single additional genetic edit to the starting line and does not require changes to the traditional Gs-based selection workflow. Continued work with cells generated by this approach, e.g., single-cell cloning, expansion, and characterization in fed-batch bioreactors, will further demonstrate the value of this system for cell line generation for biotherapeutic protein production.

Materials and Methods

Plasmid Construction. The Gs-Enbrel plasmid and Aspg-Enbrel plasmid were constructed by uracil-specific excision reagent (USER) cloning using flexible assembly sequence tags as previously described (Lund et al., 2014; Pristovšek et al., 2018). Each plasmid was generated using 4 input PCR products: 3 common inputs—a backbone, the Enbrel gene, and an early SV40 promoter—in addition to the selectable marker (Gs or Aspg). All inputs were generated via PCR amplification of DNA fragments with Phusion U Hot Start DNA polymerase (cat. no. F533S, Thermo Fisher Scientific) and uracil-containing primers (Integrated DNA Technologies, inc.). The plasmids were constructed by assembling the DNA bricks with USER Enzyme (cat. no. M5505S, New England Biolabs, Ipswich, MA) and CutSmart R Buffer (cat. no. M5505L, New England Biolabs) according to the manufacturer's protocol. Constructed plasmids were transformed into *E. coli* Mach1 competent cells (Thermo Fisher Scientific). All the constructs were verified through Sanger sequencing by Eurofins Genomics (Eurofins Scientific, Luxembourg). Two primers were used for each construct to verify the Enbrel sequence and the selection gene (Aspg or Gs). Confirmed constructs were purified using NucleoBond Xtra Midi EF kit (Macherey-Nagel) according to the manufacturer's instructions.

Cell line generation and culture maintenance. CHO-S (Life Technologies, Carlsbad, CA) cell lines were established using CRISPR/Cas9 as previously described (Gray et al., 2015) to knockout Aspg and/or Gs. The Gs/Aspg–KO was established by knocking out Aspg in the Gs–KO line. All cell lines were cultured in CD-CHO Medium (cat. No 10743029, Thermo Fisher Scientific, Waltham, MA) with 0.2% Anti-Clumping Agent (cat. no. 0010057AE, Gibco, Waltham, MA) and 8 mM glutamine unless otherwise specified. Cells were passaged every 2-3 days in 30 ml of medium in 125-ml shake flasks (Corning, Corning, NY). Viable cell densities and viabilities were measured using NUCLEOCOUNTER NC-200 or NUCLEOCOUNTER NC-250 (ChemoMetec, Allerod, Denmark). All cultures were incubated at 37° C., 80% humidity, and 5% $CO_2$; suspension cultures with working volumes >500 µl were shaken at 120 rpm.

Batch culture experiments and cell line characterization. Cells were seeded at an initial cell density of $3 \times 10^5$ cells/mL in 125 mL shake flasks (Corning) containing 30 mL medium with or without 8 mM glutamine.

Quantitative real-time polymerase chain reaction (qRT-PCR). The expression level of Gs and Aspg genes was evaluated by qRT-PCR as described previously (Kallehauge et al., 2017). Gapdh was used as a house-keeping gene in all the calculations.

96 well based minipool generation. Cells were passed into medium without Anti-Clumping Agent two days before transfection. Cells were seeded at an initial cell density of $1 \times 10^6$ cells/mL in 6-well plates. Afterward, transfection was performed with FREESTYLE MAX Reagent (cat. no. 16447100, Gibco) according to the manufacturer's protocol. After 24 h, VCD and viability of transfected cells were analyzed using NUCLEOCOUNTER NC-200. Two 96-well plates for each transfection condition were seeded with an initial cell density of 5000 cells/well. Transfected cells were seeded in cloning media (20% of CD CHO Medium+80% EX CELL CHO Cloning (Sigma-Aldrich, St. Louis, MO) with 0.2% Anti-Clumping Agent) after a previous wash step to remove all the media with glutamine.

Bulk pool generation. 24 hr after transfection, cells were seeded in 6 well plates into selection medium (without glutamine) at a cell density of $0.3 \times 10^6$ cells/mL. Every 2-3 days cells were passed or spun and resuspended into fresh selection medium until viability exceeded 90%.

Adaptation. Cells were inoculated at a concentration of $0.5 \times 10^6$ cells/mL in 125 mL flasks with 30 mL of culture medium without glutamine. Every 2-3 days, cells were passed into fresh culture medium without glutamine until the cell viability reached over 90%.

Stability testing. Cells were passed every 2-3 days at a concentration of $0.3 \times 10^6$ cells/mL in 125 mL Erlenmeyer flasks with 30 mL of culture medium without glutamine for a month. Then, batch culture was performed simultaneously for cells with and without one-month passaging time.

Titer measurement. The mAb concentration was measured using an Octet RED96 (Pall, Menlo Park, CA, USA), as described previously (Kallehauge et al., 2017).

Statistical analysis. Values are expressed as mean±standard deviation unless otherwise noted. The data were analyzed with a two-tailed Student's t-test and differences were considered statistically significant at $p<0.05$.

REFERENCES

1. Budge, J. D., Roobol, J., Singh, G., Mozzanino, T., Knight, T. J., Povey, J., Dean, A., Turner, S. J., Jaques, C. M., Young, R. J., Racher, A. J., & Smales, C. M. (2021). A proline metabolism selection system and its application to the engineering of lipid biosynthesis in Chinese hamster ovary cells. Metabolic Engineering Communications, 13, e00179.
2. Capella Roca, B., Lao, N., Barron, N., Doolan, P., & Clynes, M. (2019). An arginase-based system for selection of transfected CHO cells without the use of toxic chemicals. The Journal of Biological Chemistry, 294(49), 18756-18768.
3. Cockett, M. I., Bebbington, C. R., & Yarranton, G. T. (1990). High level expression of tissue inhibitor of metalloproteinases in Chinese hamster ovary cells using glutamine synthetase gene amplification. Bio/technology, 8(7), 662-667.
4. Grav, L. M., Lee, J. S., Gerling, S., Kallehauge, T. B., Hansen, A. H., Kol, S., Lee, G. M., Pedersen, L. E., & Kildegaard, H. F. (2015). One-step generation of triple knockout CHO cell lines using CRISPR/Cas9 and fluorescent enrichment. Biotechnology Journal, 10(9), 1446-1456.
5. Kallehauge, T. B., Li, S., Pedersen, L. E., Ha, T. K., Ley, D., Andersen, M. R., Kildegaard, H. F., Lee, G. M., & Lewis, N. E. (2017). Ribosome profiling-guided depletion of an mRNA increases cell growth rate and protein secretion. Scientific Reports, 7,40388.
6. Karottki, K. J. la C., Hefzi, H., Li, S., Pedersen, L. E., Spahn, P. N., Joshi, C., Ruckerbauer, D., Bort, J. A. H., Thomas, A., Lee, J. S., Borth, N., Lee, G. M., Kildegaard, H. F., & Lewis, N. E. (2021). A metabolic CRISPR-Cas9 screen in Chinese hamster ovary cells identifies glutamine-sensitive genes. Metabolic Engineering, 66, 114-122.
7. Kaufman, R. J., & Sharp, P. A. (1982). Amplification and expression of sequences cotransfected with a modular dihydrofolate reductase complementary dna gene. Journal of Molecular Biology, 159(4), 601-621.
8. Li, F., Vijayasankaran, N., Shen, A. (yijuan), Kiss, R., & Amanullah, A. (2010). Cell culture processes for monoclonal antibody production. In mAbs (Vol. 2, Issue 5, pp. 466-479). https://doi.org/10.4161/mabs.2.5.12720
9. Lund, A. M., Kildegaard, H. F., Petersen, M. B. K., Rank, J., Hansen, B. G., Andersen, M. R., & Mortensen, U. H. (2014). A versatile system for USER cloning-based assembly of expression vectors for mammalian cell engineering. PloS One, 9(5), e96693.
10. Noh, Soo Min, Seunghyeon Shin, and Gyun Min Lee. 2018. "Comprehensive Characterization of Glutamine Synthetase-Mediated Selection for the Establishment of Recombinant CHO Cells Producing Monoclonal Antibodies." *Scientific Reports* 8 (1): 5361.
11. Pourcel, L., Buron, F., Garcia, F., Delaloix, M.-S., Le Fourn, V., Girod, P.-A., & Mermod, N. (2020). Transient vitamin B5 starving improves mammalian cell homeostasis and protein production. Metabolic Engineering, 60, 77-86.
12. Pristovšek, N., Hansen, H. G., Sergeeva, D., Borth, N., Lee, G. M., Andersen, M. R., & Kildegaard, H. F. (2018). Using Titer and Titer Normalized to Confluence Are Complementary Strategies for Obtaining Chinese Hamster Ovary Cell Lines with High Volumetric Productivity of Etanercept. Biotechnology Journal, 13(3), e1700216.
13. Sun, T., Kwok, W. C., Chua, K. J., Lo, T.-M., Potter, J., Yew, W. S., Chesnut, J. D., Hwang, I. Y., & Chang, M. W. (2020). Development of a Proline-Based Selection System for Reliable Genetic Engineering in Chinese Hamster Ovary Cells. ACS Synthetic Biology, 9(7), 1864-1872.
14. Walsh, Gary. 2018. "Biopharmaceutical Benchmarks 2018." *Nature Biotechnology* 36 (12): 1136-45.
15. Zhang, Q., Jiang, B., Du, Z., & Chasin, L. A. (2020). A doubly auxotrophic CHO-K1 cell line for the production of recombinant monoclonal antibodies. Biotechnology and Bioengineering, 117(8), 2401-2409.
16. Zhang, Q., Jiang, B., Nelson, L., Huhn, S., Du, Z., & Chasin, L. A. (2022). A multiauxotrophic CHO cell line for the rapid isolation of producers of diverse or high levels of recombinant proteins. Biotechnology and Bioengineering. https://doi.org/10.1002/bit.28074.

What is claimed is:

1. A non-naturally occurring mammalian cell comprising an inoperative genomic asparaginase (Aspg) gene and an inoperative glutamine synthetase (Gs) gene, wherein the cell has been transfected with a controllably expressed gene encoding an enzyme with asparaginase activity, a controllably expressed gene encoding an enzyme with glutamine synthetase activity, and a controllably expressed gene encoding a heterologous protein.

2. The cell of claim 1, wherein the cell has been immortalized.

3. The cell of claim 1, wherein the cell is a Chinese hamster ovary (CHO) cell.

4. The cell of claim 1, wherein the cell is an Aspg and Gs double knock-out made with a CRISPR-Cas9 system.

5. The cell of claim 1, wherein the gene encoding an enzyme with asparaginase activity is an Aspg gene, the gene encoding an enzyme with glutamine synthetase activity is a Gs gene, or both.

6. The cell of claim 5, wherein the Gs gene and the Aspg gene are transfected into the cell on separate plasmids, and wherein each plasmid further comprises the gene encoding the heterologous protein.

7. The cell of claim 1, wherein the gene encoding the enzyme with glutamine synthetase activity is a Glul gene.

8. A selection system for heterologous protein expression in cells, comprising a non-naturally occurring mammalian cell comprising an inoperative genomic asparaginase (Aspg) gene and an inoperative glutamine synthetase (Gs) gene, wherein the cell has been transfected with a controllably expressed gene encoding an enzyme with asparaginase activity, a controllably expressed gene encoding an enzyme with glutamine synthetase activity, and a controllably expressed gene encoding a heterologous protein; and
a medium which contains substantially no glutamine.

9. The system of claim 8, wherein the cell has been immortalized.

10. The system of claim 8, wherein the cell is a Chinese hamster ovary (CHO) cell.

11. The system of claim 8, wherein the cell is an Aspg and Gs double knock-out made with a CRISPR-Cas9 system.

12. The system of claim 8, wherein the gene encoding an enzyme with asparaginase activity is an Aspg gene, the gene encoding an enzyme with glutamine synthetase activity is a Gs gene, or both.

13. The system of claim 12, wherein the Gs gene and the Aspg gene are transfected into the cell on separate plasmids, and wherein each plasmid further comprises the gene encoding the heterologous protein.

14. The system of claim 8, wherein the gene encoding an enzyme with glutamine synthetase activity is a Glul gene.

15. The system of claim 8, wherein the medium is supplemented with a glutamine synthetase expression medium (GSEM) supplement.

16. The system of claim 8, wherein the cell is in a suspension culture.

17. A method of expressing a heterologous protein comprising expressing the heterologous protein with the cell of claim 1.

18. The method of claim 17, wherein the heterologous protein is an active pharmaceutical ingredient, a reagent in an industrial process, or an ingredient in a diagnostic reagent.

19. A method of preparing a non-naturally occurring mammalian cell for production of a heterologous protein, comprising:
a) contacting a mammalian cell with a gene editing system configured to inactivate an asparaginase (Aspg) gene and a glutamine synthetase (Gs) gene; and
b) transfecting the mammalian cell or a descendent of the mammalian cell with:
i) a first plasmid comprising a controllably expressed gene encoding an enzyme with asparaginase activity and a first controllably expressed gene encoding the heterologous protein; and
ii) a second plasmid comprising a controllably expressed gene encoding an enzyme with glutamine synthetase activity and a second controllably expressed gene encoding the heterologous protein.

20. The method of claim 19, further comprising a step of c) placing the transfected mammalian cell into a medium which contains substantially no glutamine.

* * * * *